United States Patent [19]

Braithwaite

[11] 4,322,532

[45] Mar. 30, 1982

[54] SOLVENTS FOR THE CATALYTIC PRODUCTION OF ACRYLAMIDE FROM ACRYLONITRILE AND WATER

[75] Inventor: David G. Braithwaite, Tyler, Tex.

[73] Assignee: Nalco Chemical Company, Oak Brook, Ill.

[21] Appl. No.: 207,521

[22] Filed: Nov. 17, 1980

[51] Int. Cl.³ .............................................. C07C 102/08
[52] U.S. Cl. ..................................... 546/128; 546/126; 546/127
[58] Field of Search .......................... 546/126, 127, 128

[56] References Cited

U.S. PATENT DOCUMENTS

| | | | |
|---|---|---|---|
| 3,381,034 | 4/1968 | Greene et al. | 564/127 |
| 3,597,481 | 8/1971 | Tefertiller et al. | 564/127 |
| 3,631,104 | 12/1971 | Habermann et al. | |
| 3,670,021 | 6/1972 | Goetz et al. | |
| 3,674,848 | 7/1972 | Schoenbrunn et al. | |
| 3,679,745 | 7/1972 | Schoenbrunn | |
| 3,686,307 | 8/1972 | Greene et al. | |
| 3,696,152 | 10/1972 | Habermann et al. | |
| 3,758,578 | 9/1973 | Habermann et al. | |
| 3,767,706 | 10/1973 | Habermann et al. | |
| 3,920,740 | 11/1975 | Svarz et al. | |
| 3,997,606 | 12/1976 | Kane | 564/127 |

FOREIGN PATENT DOCUMENTS

| | | |
|---|---|---|
| 899380 | 5/1972 | Canada . |
| 930377 | 7/1973 | Canada . |
| 551869 | 6/1932 | Fed. Rep. of Germany . |
| 41-21295 | 5/1966 | Japan . |
| 47-33327 | 8/1972 | Japan . |
| 48-36118 | 5/1973 | Japan . |
| 48-39424 | 6/1973 | Japan . |
| 48-39426 | 6/1973 | Japan . |
| 48-54021 | 7/1973 | Japan . |
| 967585 | 8/1964 | United Kingdom . |

OTHER PUBLICATIONS

"Catalyzed Hydration of Nitriles to Amides," *Ind. Eng. Chem. Prod. Redevelop.*, vol. 11, No. 3, 1972, pp. 364, 365.

"Studies on Organic Catalytic Reactions. II. The Hydration of Nitrile to Amides with Nickel Catalysts," by Watanabe, *Bull. Chem. Soc.*, Japan 37 (1964), pp. 1325-1329.

*Primary Examiner*—Arthur P. Demers
*Attorney, Agent, or Firm*—John G. Premo; Robert A. Miller

[57] ABSTRACT

A method of catalytically converting acrylonitrile and water with a metallic conversion catalyst into pure acrylamide crystals.

3 Claims, No Drawings

SOLVENTS FOR THE CATALYTIC PRODUCTION OF ACRYLAMIDE FROM ACRYLONITRILE AND WATER

INTRODUCTION

It is now known that dry acrylamide can be produced by using the teachings of U.S. Pat. No. 3,997,606. The technology disclosed in this patent is summarized in the specification as follows:

"In accordance with my invention, it has been discovered that dry acrylamide is readily produced by reacting acrylonitrile with from 0.3 to 1 mole of water in the presence of a metallic nitrile conversion catalyst under conditions including the use of elevated temperature and pressure whereby at least 30% by weight of the nitrile is converted to acrylamide. The acrylamide at this point in my process is in the form of a solution within the nitrile-water mixture. Upon release of the pressure which includes the use of vacuum and/or with cooling, the acrylamide crystallizes from the reaction mixture and may be readily removed therefrom. These crystals are characterized as containing 0.5% by weight or less of acrylonitrile and less than 5% by weight of water."

The disclosure of this patent is incorporated herein by reference.

This patent provides an improved method for producing substantially dry polyacrylamide from acrylonitrile and water. As pointed out by the patentee, prior processes required expensive evaporation techniques since the acrylamide in prior art catalytic processes was produced as a solution.

One of the disadvantages set forth in U.S. Pat. No. 3,997,606 is that the finished product contains small quantities of impurities such as acrylonitrile.

If it were possible to produce dry acrylamide of high purity without necessitating an evaporative procedure, an advance in the art would be afforded. Also of benefit would be a process whereby the temperature of the reaction could be controlled and elevated pressures would not be required for maintaining the acrylonitrile in a liquid state. Of further benefit would be a process which would allow easy recovery of the produced acrylamide free from unwanted byproducts.

THE INVENTION

An improved method for producing acrylamide comprising reacting a DETEG (diethyl ether of tetraethylene glycol) solution of acrylonitrile and water in the presence of a metallic nitrile conversion catalyst under conditions which convert at least a portion of the acrylonitrile to acrylamide and then recovering the acrylamide.

The Metallic Nitrile Conversion Catalyst

During the last several years, numerous metallic catalysts for converting nitrile and water into amides have been patented or described in the literature. A summary of these catalysts as well as literature references thereto is set forth below:

| Catalyst | Literature Reference |
|---|---|
| Raney copper, Ullman copper, reduced copper, copper on a carrier, silver cobalt, nickel, palladium and platinum. Copper in combination with nickel, chromium, manganese, zinc, molybdenum, as well as oxides or sulfides of said metal. | Canadian Patent 899,380 Canadian Patent 930,377 |
| Combinations consisting essentially of 10 to 90% by weight of oxides of copper silver, zinc or cadmium and 10 to 90% by weight of oxides of chromium or molybdenum. | U.S. Pat. No. 3,597,481 |
| Urushibara - copper chloride precipitate with zinc dust. | Watanabe in Bull. Chem. Soc. Japan, 37, 1325 (1964) |
| Copper, Copper oxide, copper-chromium oxide, copper-molybdenum oxide or mixtures thereof. | U.S. Pat. No. 3,631,104 |
| Reduced copper oxides in combination with other metal oxides, particularly rare earth metal oxides. | U.S. Pat. No. 3,696,152 |
| Copper prepared by reducing copper hydroxide or a copper salt. | U.S. Pat No. 3,758,578 |
| Copper metal. | U.S. Pat. No. 3,767,706 |
| Highly active Raney copper. | U.S. Pat. No. 3,920,740 |
| Zinc and cadmium oxides. | German 551,869 |
| Lithium hydroxide. | U.S. Pat. No. 3,686,307 |
| Ruthenium, rhodium, palladium, osmium, iridium or platinum. | U.S. Pat. No. 3,670,021 |
| Fatty acid salts of cadmium, zinc, copper, cobalt, lead, tin, titanium, nickel, iron, mercury; sulfates, nitrates and halides of lead, tin, titanium, nickel, iron, mercury; tin, cadmium and copper oxides; copper powders. | Jap. 70/21, 295. Inoue et al., Ashi Kasei Co., 7-18-70. |
| Cupric hydroxide, manganese dioxide, chromium, tungsten, iron or nickel oxide. | Japan 72/33,327 |
| Boron hydroxide and inorganic phosphorous containing acids. | Japan 73/36118 |
| Cobalt chromium catalyst. | Japan 73/39424. |
| Nickel chromium catalyst. | Japan 73/39426 |
| Ruthenium or rhodium. | Japan 73/54,021 |
| Manganese dioxide. | Haefele et al., Ind. Eng. Chem. Prod. Res. Develop. 11(3), 364–365 (1972) |
| Zinc, copper, cobalt and cadmium thiocyanates, sulfates, nitrates, halides and cyanides as well as metallic zinc and metallic copper. | Spanish Patent Application Public No. 695205 |
| Metal salts of cation exchange resins. | U.S. Pat. No. 3,674,848 |
| Cuprous hydrogen phosphate. | U.S. Pat. No. 3,679,745 |
| Cuprous salts and cupric salts. | U.S. Pat. No. 3,381,034 |

Of the above catalysts, it is preferred to use in the practice of this invention a special Raney copper catalyst which contains from about 2 to 45% by weight of aluminum. This catalyst in its preferred embodiment contains particles having an average particle diameter ranging from 0.002 to 0.5 inches and has a relative activity of at least about 2. Catalysts of this type as well as their method of preparation are disclosed in U.S. Pat. No. 3,920,740, the disclosure of which is incorporated herein by reference.

The Reaction Conditions

It is beneficial to use from between 0.3 to 1 mole of water per mole of nitrile during the conversion of the nitrile to the acrylamide. Preferably, between 0.35 to 1 mole of water per mole of acrylonitrile may be used. Larger amounts of water may be used.

With respect to the various temperatures and pressures that may be used as well as the quantity of catalyst, flow rates and the like, reference may be had to U.S. Pat. No. 3,920,740 as well as the teachings of U.S. Pat. No. 3,767,706. As indicated in this latter reference, the temperatures may range in a preferred mode of operation between 25°–200° C.

The pressure may be as low as 15 lbs./sq. in. up to as high as 200 lbs./sq. in. If the catalyst is a solid and used in a fixed bed operational scheme, the flow rate can vary widely depending on the activity of the catalyst, the temperature and the pressure. A routine experimentation can determine optimum flow rates based on the other parameters discussed, particularly in view of the teachings of U.S. Pat. No. 3,920,740.

While high pressures may be used, they are not necessary since the DETEG allows the reaction to be conducted in a liquid environment, thus making low reaction temperatures feasible and reaction control a simple matter.

The solvent, DETEG, used in the practice of the invention is the diethyl ether of tetraethylene glycol. It is a solvent for both the acrylonitrile and the water. Hot, it is a solvent for the acrylamide although upon cooling, a substantial portion of the acrylamide tends to precipitate therefrom. The amount of DETEG used is that amount sufficient to dissolve the reactants and still maintain the reaction media liquid.

A preferred mode of this invention resides in precipitating the acrylamide from the DETEG solution by treating the solution with a hydrocarbon liquid. A preferred hydrocarbon liquid is an aromatic hydrocarbon liquid such as toluene.

To illustrate the invention, the following are presented by way of example:

EXAMPLE 1

202 g. acrylonitrile
30 g. water
200 g. DETEG
53 g. Raney copper (U.S. Pat. No. 3,920,740)

This charge was reacted overnight at 100° C. Toluene was added to product. This gave 81 g. of crystals which, after washing with toluene and drying, analysed 19.7% nitrogen (100% of theoretical)

EXAMPLE 2

405 g. acrylonitrile
300 g. DETEG
45 g. water
121 g. wet catalyst

This was reacted at 125° C. for 6 hours. Acrylamide crystals precipitated from the reaction mixture upon cooling without addition of hydrocarbon. These acrylamide crystals were washed with toluene and dried by suction.

Having thus described my invention, it is claimed as follows:

1. An improved method for producing dry acrylamide of high purity comprising reacting a diethyl ether of tetraethylene glycol solution of acrylonitrile and water in the presence of a metallic nitrile conversion catalyst under conditions which convert at least a portion of the acrylonitrile to acrylamide and then recovering the acrylamide by treating the solution with a hydrocarbon liquid and recovering the precipitated dry acrylamide.

2. The method of claim 1 where the catalyst is a Raney copper catalyst which contains from about 2 to 45% by weight of aluminum.

3. The method of claim 1 wherein the hydrocarbon liquid is toluene.

* * * * *